United States Patent [19]
Koizumi et al.

[11] Patent Number: 5,277,182
[45] Date of Patent: Jan. 11, 1994

[54] CORONORY ARTERY IMAGING METHOD AND APPARATUS

[75] Inventors: Hideaki Koizumi, Katsuta; Ryuzaburo Takeda, Mito; Hideki Kohno, Tama; Tetsuo Yokoyama, Tokyo; Yoshiyuki Miyamoto, Katsuta; Koichi Sano, Sagamihara, all of Japan

[73] Assignee: Hitachi, Ltd., Tokyo, Japan

[21] Appl. No.: 723,692

[22] Filed: Jun. 24, 1991

Related U.S. Application Data

[63] Continuation of Ser. No. 322,992, Mar. 14, 1989, abandoned.

[30] Foreign Application Priority Data

Mar. 14, 1988 [JP] Japan ................................. 63-60013

[51] Int. Cl.$^5$ ............................................. A61B 5/055
[52] U.S. Cl. ................................. 128/653.3; 128/708
[58] Field of Search .................. 128/653.2, 653.3, 708; 324/306, 309

[56] References Cited

U.S. PATENT DOCUMENTS

| | | | |
|---|---|---|---|
| 4,595,879 | 6/1986 | Lent et al. | 324/306 |
| 4,739,766 | 4/1988 | Riederer | 128/653 AF |
| 4,777,957 | 10/1988 | Wehrli et al. | 128/653 AF |
| 4,836,209 | 6/1989 | Nishimura et al. | 128/653.3 |
| 4,855,910 | 8/1989 | Bohning | 364/413.13 |
| 4,895,157 | 1/1990 | Nambu | 128/653 A |

OTHER PUBLICATIONS

Proceedings of the International Symposium CAR '87, pp. 66-73.

Primary Examiner—Ruth S. Smith
Attorney, Agent, or Firm—Antonelli, Terry, Stout & Kraus

[57] ABSTRACT

A method for imaging the coronary artery of a living body using nuclear magnetic resonance, wherein a patient is located in a static magneic field and the heart cycle of the patient is detected with the heart dilation period of the patient being determined in accordance with the detected heart cycle. Then, the coronary artery of the patient is portrayed on the nuclear magnetic resonance signal generated by applying high-frequency energy to the patient during the determined heart dilation period.

20 Claims, 5 Drawing Sheets

CORONORY ARTERY IMAGING METHOD AND APPARATUS

This application is a continuation of application Ser. No. 322,992, filed Mar. 14, 1989 now abandoned.

BACKGROUND OF THE INVENTION (1) Field of the Invention

The present invention relates to a coronary artery imaging method and apparatus, and more particularly to a method for noninvasively imaging a coronary artery using a nuclear magnetic resonance phenomenon.

(2) Description of Prior Art

X-ray angiography is a typical coronary artery imaging method. This method employs an iodine contrast agent and includes the steps of inserting a catheter into a coronary artery from a foot artery to thereby inject the contrast agent into a coronary artery through the catheter and imaging the coronary artery on the basis of absorption of x-rays by the contrast agent.

Of late, this type of coronary artery imaging method has been frequently employed for pre-detecting heart diseases such as heart attack or myocardial infarction, which have recently been increasing.

The foregoing coronary artery imaging method requires an operation to insert the catheter into a foot artery. In the operation, the catheter must be handled carefully to avoid damaging the artery. Furthermore this method is hazardous, because much of the contrast agent must be administered for a short time.

SUMMARY OF THE INVENTION

An object of the present invention is to provide a coronary artery imaging method and apparatus which employ a nuclear magnetic resonance phenomenon.

Another object of the invention is to provide a method and apparatus which are appropriate for imaging the coronary artery noninvasively.

This invention includes the steps of locating a living body in a static magnetic field and detecting the cardiac cycle of the living body. Then, the detected body's cardiac cycle is used to determine the dilation time of the heart or the time when the difference in a given parameter between the blood in the coronary artery and that outside of it substantially reaches a maximum value. The coronary artery of the living body is portrayed by a nuclear magnetic resonance signal, which is generated from the living body by applying high-frequency energy to the living body during the determined time in the presence of a magnetic field gradient.

These and other objects and features of this invention will be apparent from the following description in conjunction with the drawings.

DESCRIPTION OF PREFERRED EMBODIMENT

Before the actual description of an embodiment, reference is directed to the process by which this invention has been completed.

The anatomical features of the blood flowing through the coronary artery are explained below referring to FIG. 1.

Figure 1A:
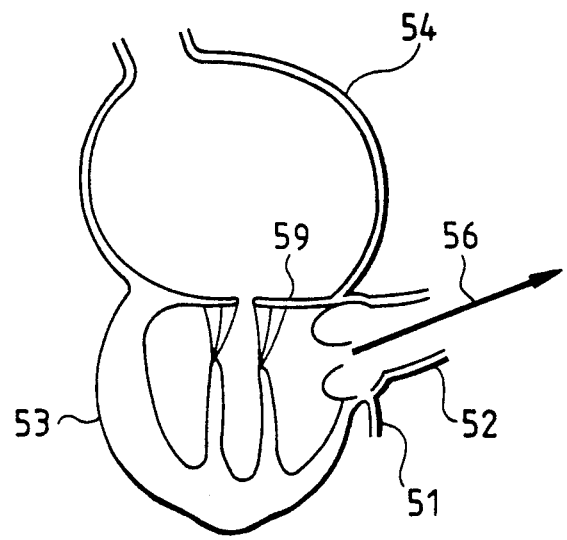
FIG. 1(A) is a sectional view of the heart of a living body when contracted and FIG. 1(B) is a sectional view of the heart of the living body when it is dilated.
Figure 1B:
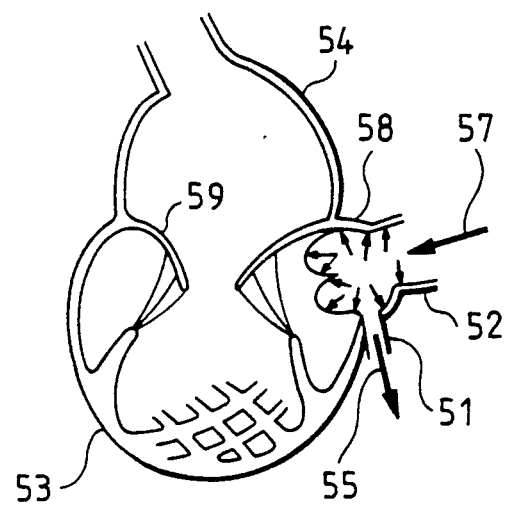

FIG. 1(A) shows the state in the heart contraction period, and FIG. 1(B) shows the state in the heart dilation period. As shown in FIG. 1(A), when the left ventricle 53 communicating with the atrium 54 is contracted, the main artery valve 59 is opened and the blood is ejected of discharged into the main artery 52. Then, as shown in FIG. 1(B), when the left ventricle 53 is dilated, the main artery valve 59 is closed and the blood counterflows (57) into the main artery 52 and spreads out the main artery cavity or aortic sinus 58. At that time, the inlet of the coronary artery is widened so that the blood flows into the coronary artery 51. Under the state shown in FIG. 1(A), the blood does not flow so much into the coronary artery 51, which is substantially perpendicular to the main artery 52. That is, the heart pulse phase caused when the blood flows into an ordinary artery is different from that when the blood flows into the coronary artery. It means that physical parameters such as velocity, direction, or acceleration of the blood flowing through a normal artery, ventricle, or atrium differ greatly from those of the blood flowing through the coronary artery.

Figure 2:
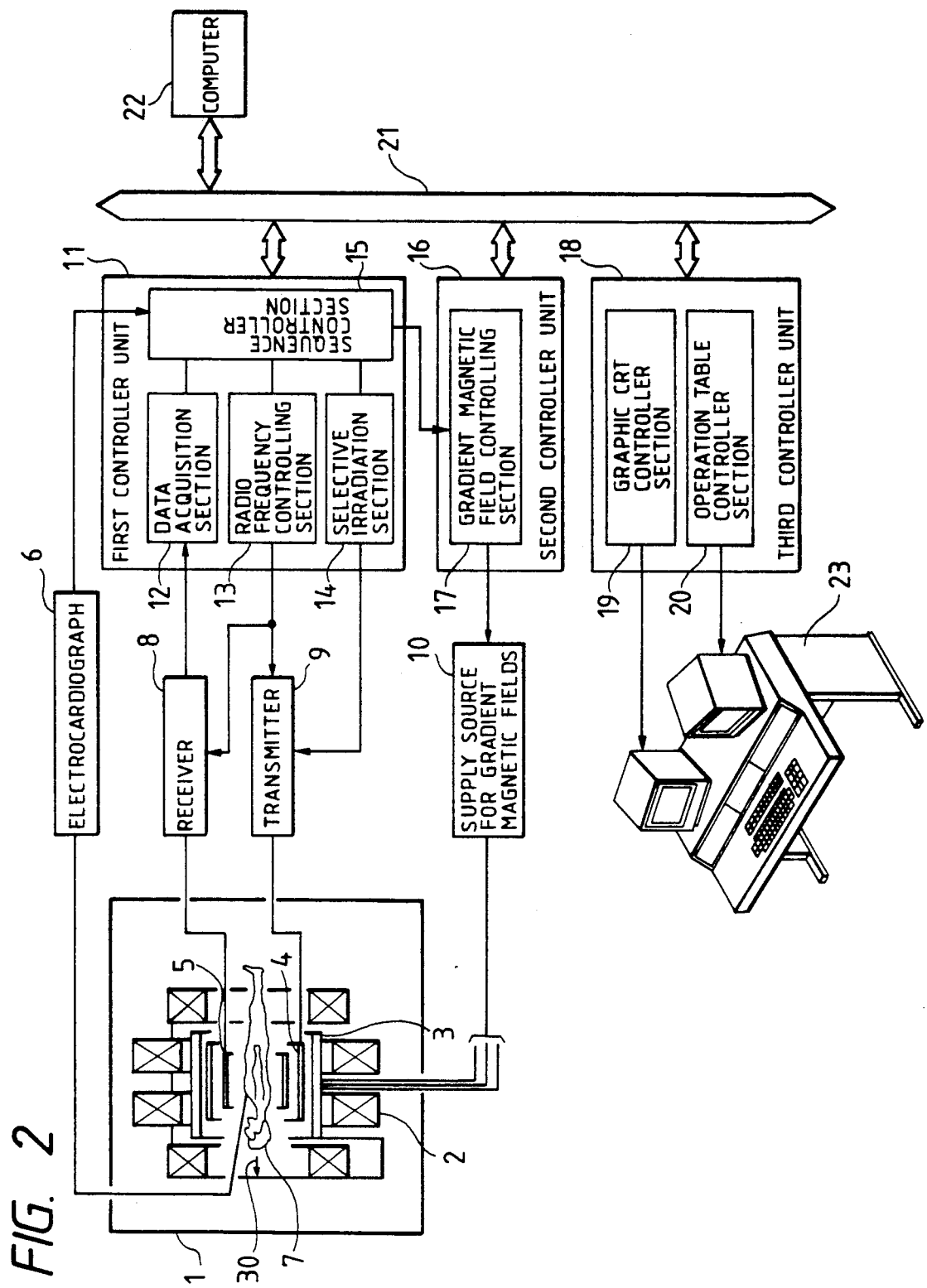
FIG. 2 is a block diagram of a nuclear magnetic resonance imaging system in accordance with the present invention.

This invention is based on the above knowledge and reference is made to FIG. 2 which illustrates an embodiment in accordance with the present invention wherein a main body 1 of the magnetic resonance imaging system includes four electromagnets 2 for forming a static magnetic field, a gradient magnetic field coil 3 for forming magnetic field gradients, an irradiation coil 4 for irradiating a 90° or 180° pulse as high-frequency or radio-frequency energy, and a receiving coil 5 for receiving a nuclear magnetic resonance signal. The direction 30 of the static magnetic field is normally assumed to be a z-axis as shown by the arrow in FIG. 2. The gradient magnetic field coil 3 includes three X, Y, and Z coils so that independent magnetic field gradients are produced in each direction of X, Y and Z.

Within these coils is located a living body 7 whose coronary artery is to be imaged. An electrocardiograph 6 is mounted on the living body 7.

The receiving coil 5 is connected to a receiver 8. The irradiation coil 4 is connected to a transmitter 9. A first controller unit 11 includes a data acquisition section 12, a radio-frequency controlling section 13, a selective irradiation section 14, and a sequence controller section 15. The data acquisition section 12 is connected to the receiver 8, and the radio-frequency controlling section 13 and the selective irradiation section 14 are connected to the transmitter 9. The sequence controller section 15 is individually connected to the data acquisition section 12, the radio-frequency controlling section 13, and the selective irradiation section 14. Furthermore, the electrocardiograph 6 is connected to the sequence controller section 15.

A second controller unit 16 includes a gradient magnetic field controlling section 17, which is connected to the sequence controller section 15 and the supply source for gradient magnetic fields 10.

A third controller unit 18 includes a graphic CRT controller section 19 and an operation table controller section 20 connected to a console 23.

The controller units 11, 16, and 18 are connected to a computer 22 through a bus 21.

The electromagnet 2 may be any one of a superconductivity type magnet, a normal conductivity magnet, or a permanent magnet. This embodiment employs a normal conductivity magnet. This type of magnet normally employs a hollow electromagnet to provide a highly uniform magnetic field. In this embodiment, the magnetic flux density is 0.15 T (tesla) and the magnetic field uniformity is about 50 ppm/30 cm dsv (sphere).

Next, the operation of this embodiment is described.

The electromagnets 2 located inside of the main body 1 form a static magnetic field. The current is supplied from a static magnetic field supply source. A patient or living body 7 is laid on a table and is positioned at the center of the electromagnets 2 and a 90° or 180° pulse from the transmitter 9 is applied to the patient by the irradiation coil 4. The frequency of the pulse is selected by the selective irradiation section 14 controlled by the sequence controller section 15. The supply source for gradient magnetic fields 10 includes a constant current power source having three channels for independently generating the three gradient magnetic fields in the x-axis, y-axis, and z-axis directions. When the gradient magnetic fields are applied to the static magnetic field to provide spatial position information, they are pule-like and thus require a fast response.

A nuclear magnetic resonance (NMR) signal is generated from the patient when radio frequency energy is applied to the patient. The signal is detected by the receiving coil 5 and supplied to the receiver 8. The receiver 8 and the transmitter 9 are precisely synchronized in phase by applying a receiver gate thereto, because phase information for the NMR signal is important.

Blood velocity is selected among physical parameters to image the coronary artery. The controller units 11 and 16 perform sequence control to portray the coronary artery using the difference in the selected physical parameter.

The console 23 is used for operating the system. It is equipped with various keys and two CRTs. One CRT is used for interactively setting various physical parameters. The other CRT is used for displaying the image.

The computer 22 is responsible for the high-speed operation to control the overall system and form an image. It communicates with each control system through the bus 21. The sequence controller section 15 is responsible for controlling various pulse sequences, but the main pulse sequence is relevant to the combination of a high-frequency pulse and a gradient magnetic field pulse.

Figure 3:
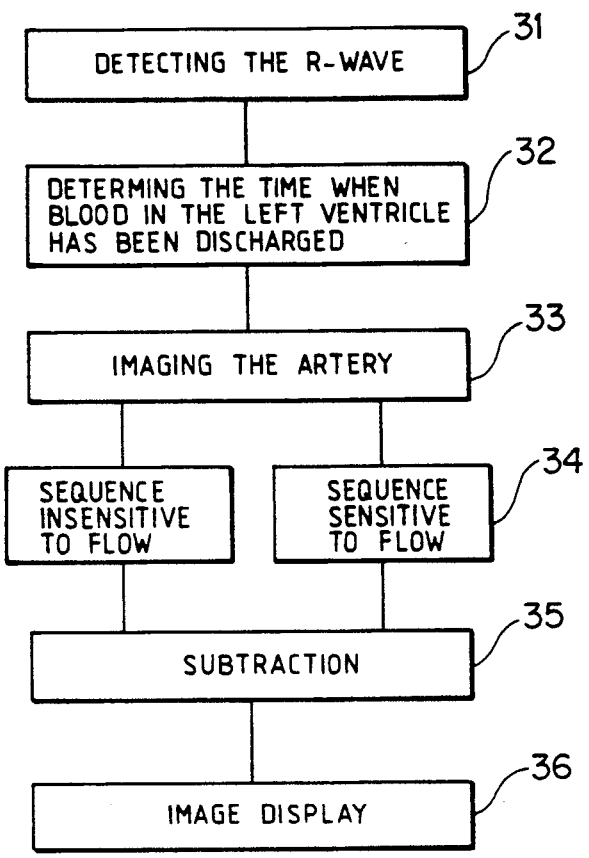
FIG. 3 is a flow chart in accordance with the present invention.
Figure 4:
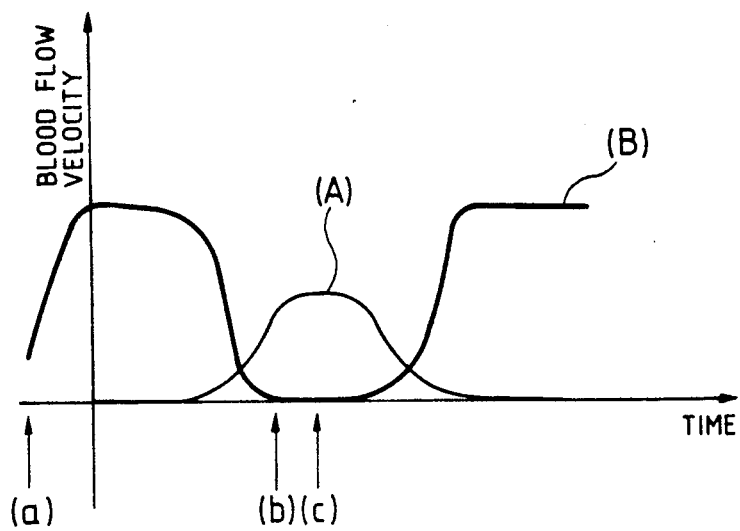
FIG. 4 is a graph showing a relation between velocities of blood flow within and outside of the coronary artery.

Next, reference is directed to a general description of the sequence control. FIG. 3 is an explanatory view outlining a measuring method for portraying the stressed coronary artery, depending upon the difference of a flow velocity of the blood flowing through the coronary artery and the heart. FIG. 4 is a graph showing the difference in blood velocity between the blood in the coronary artery (A) and that in the left ventricle of the heart (B).

As shown in FIG. 3, in step 31 the R-wave on an electrocardiogram is detected by the electrocardiograph 6 shown in FIG. 2. The timing at this step corresponds to (a) in FIG. 4.

In step 32 the time when the left ventricle of the heart has been discharged is determined on the basis of the R-wave. This time point corresponds to (b) in FIG. 4.

Then, step 33 images the coronary artery. The timing at this step corresponds to (c) in FIG. 4. That is, the proper imaging time is the heart pulse phase time when the velocity difference between the blood in the coronary artery and that in the left ventricle of the heart reaches a maximum point.

In this embodiment, two sequences are formed, that is, one sequence which is sensitive to the flow of the blood flow velocity and the other sequence which is insensitive to the flow. Step 34 in FIG. 3 images the coronary artery using the flow-insensitive sequence and the flow-sensitive sequence.

The step 35 substracts the NMR signal sent from the flow-insensitive sequence from the NMR signal sent from the flow-sensitive sequence. The resulting difference is useful for suppressing the NMR signal from the heart core and stressing the NMR signal from the coronary artery, resulting in the imaging of the coronary artery.

In step 36 an image of the coronary artery is displayed on the graphic CRT equipped on the console 23 in FIG. 2.

The time when blood in the left ventricle of the heart has been discharged is determined on the electrocardiogram which is obtained from the sequence controller section 15 through the bus 21. Likewise, the timing when the coronary artery is imaged is determined on the electrocardiogram.

Next, reference is directed to details of the sequence for portraying the coronary artery as described in this embodiment.

At first, a description will be given of the imaging method using the NMR phenomenon, which is relevant to this embodiment.

Figure 5:
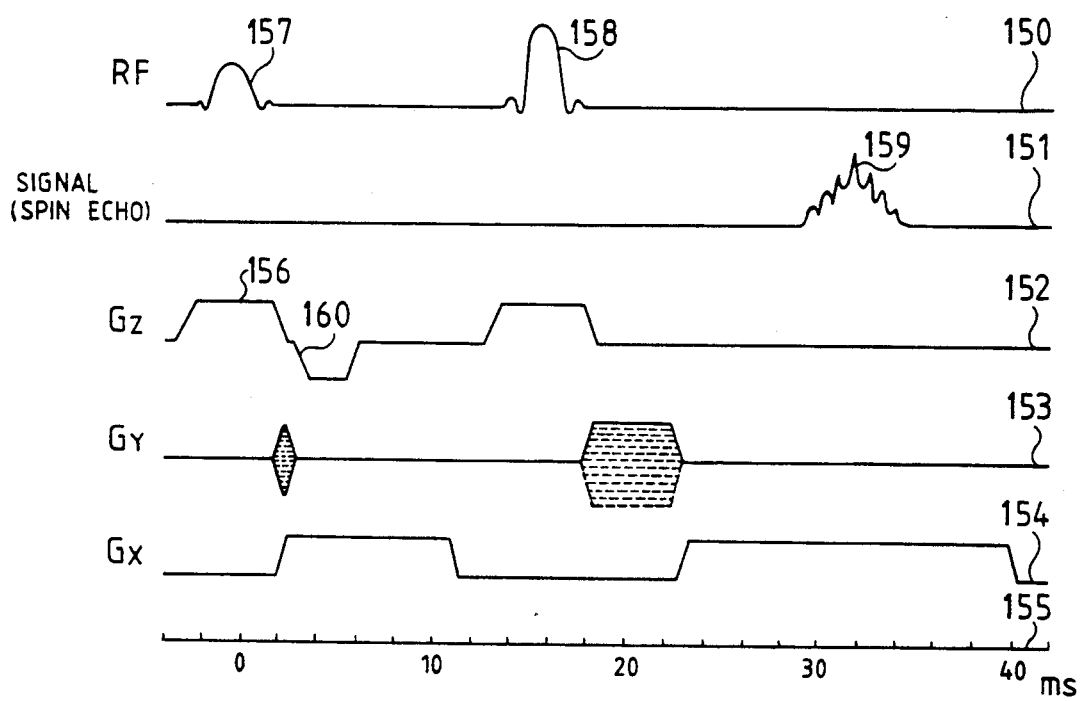
FIG. 5 illustrates a pulse sequence in accordance with the present invention.

FIG. 5 shows one example of a pulse sequence for imaging. The topmost waveform in FIG. 5 denotes a radio or high-frequency wave 150, that is, a pulse waveform of a high-frequency power irradiated from the irradiation coil to the patient. A signal 151, shown below the wave 150, is the amplified electromotive force which is generated in the receiving coil. A gradient magnetic field 152 denotes a magnetic field gradient applied to the direction of the static magnetic field. A gradient magnetic field 153 encodes the phase in the y-axis direction. A gradient magnetic field 154 corresponds to the coordinate in the x-axis direction with the frequency. It is, in general, used for generating a spin echo and thus may be interpreted as a reading magnetic field gradient. A time axis 55 clarifies the relation between the time and all the pulse sequences shown above in FIG. 5.

Next, reference is directed to a detailed description of a role of each pulse and the principle of two-dimension Fourier transform image reconstruction.

In the example shown in FIG. 5, a Sinc function is used for representing the waveform of a high-frequency pulse. The Sinc function can be Fourier-transformed into a square waveform presenting the waveform of a high-frequency pulse. That is, a sinc function in a time domain results in a square waveform in a frequency domain which is provided with a limited frequency area. In FIG. 5, a magnetic field gradient pulse 156 is applied when applying a 90° pulse (meaning a pulse for tipping the nuclear spins 90°). Since the resonance conditions in the NMR phenomenon are represented by the following equation, a particular slice in the z-axis direction is selectively excited.

$$\omega 0 - \gamma[H_O + H_G(Z)] \quad (1)$$

where $\omega$ denotes the angular velocity at a resonant point, denotes a gyro magnetic ratio, $H_O \gamma$ denotes the magnetic flux density of a static magnetic field, and $H_G(Z)$ denotes the magnetic flux density of a gradient magnetic field in position Z.

The normal NMR imaging assumes that the slice is 1 to 20 mm thick when it sets a selective irradiation frequency. In this embodiment, a spin echo signal 159 is obtained by applying a 90° pulse 157 followed by a 180° pulse 158.

A spin echo technique is used for rephasing a phase which has rapidly dispersed by an inhomogeneous magnetic field for an apparent transverse relaxation time $T_2$. To obtain a signal having a rephased phase, it is necessary to reverse the magnetic field gradient or apply the 180° pulse 158 together with the magnetic field gradient. The later half-section of the magnetic field gradient 156 causes the spin to be dephased. To compensate for dephasing, a gradient magnetic field pulse 156 is applied followed by a compensating pulse 160.

Next, reference is directed to a description of phase encoding. The fundamental elements of nuclear spin behavior in the NMR phenomenon are: 1. Direction of a magnetic moment, 2. Magnitude of a magnetic moment, 3. Number of magnetic moments, 4. Frequency of a magnetic moment, and 5. Phase of a magnetic moment. As a statistical result of individual parameters, the microscopic effect of magnetization can be descriptive. In particular, by encoding the phase because of their independence, it is possible for frequency and phase parameters to correspond with the space coordinate. The magnetic field gradient 153 in FIG. 5 encodes the phase. Since the quantity of phase encoding is determined by an integral value of an encoding magnetic field gradient pulse, for encoding the phase, it is necessary to change the amplitude or width of a pulse. The amplitude change is shown n FIG. 5.

Since the magnetic field gradient 154 is applied immediately after the application of the 90° pulse, it dephases the spins. However, considering that the magnetic field gradient 54 is applied when an echo signal is read, the spins are rephased so that a strong spin echo signal is generated. The x-coordinate has a linear relation with a resonance frequency. To obtain the relation between the signal intensity and the x-coordinate, therefore, the spin echo signal 159 is Fourier-transformed for time. The result should be further Fourier-transformed to obtain the relation between the signal intensity and the y-coordinate. As a result, the signal intensity distribution on the x-y plane is obtained. When signal intensity is displayed on th CRT, therefore, a slice image can be obtained.

Figure 6A:
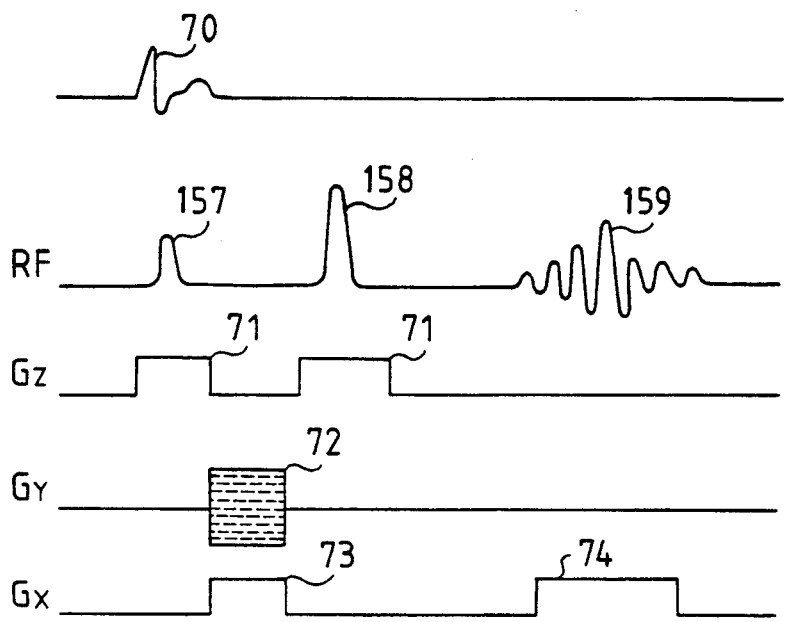
FIG. 6(A) illustrates a pulse sequence in accordance with the present invention which is sensitive to the blood flow velocity and FIG. 6(B) illustrates a pulse sequence in accordance with the present invention which is insensitive to the blood flow velocity.
Figure 6B:
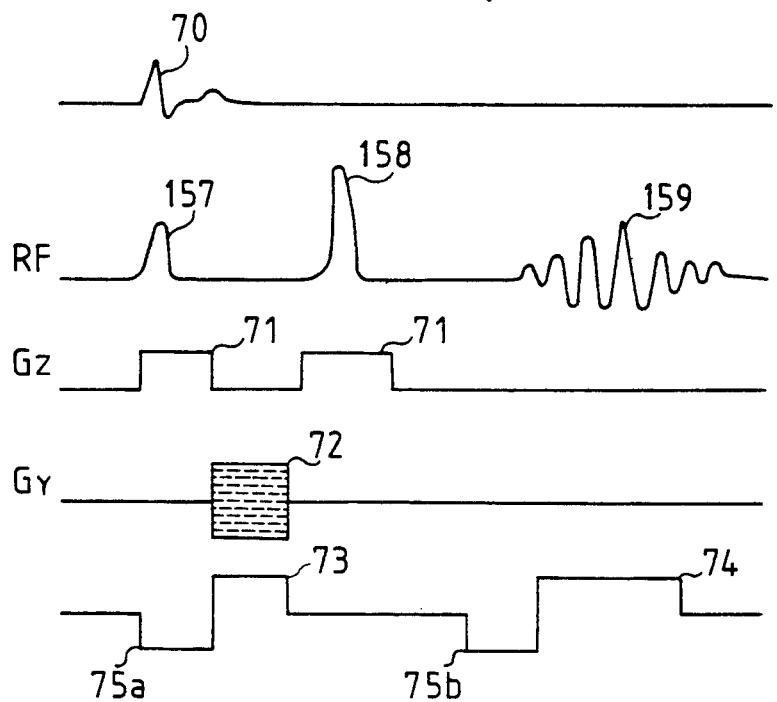

Next, reference is directed to details of a pulse sequence according to this embodiment. FIGS. 6(A) and 6(B) are a detailed view of the sequence.

FIG. 6(A) denotes a sequence that is sensitive to the blood flow velocity and FIG. 6(B) denotes a sequence that is insensitive to the blood flow velocity.

The R-wave on an electrocardiogram is denoted by 70. It is supplied from the electrocardiograph 6 to the sequence controller section 15 and is used for determining the control timing of a pulse signal for obtaining the coronary artery image.

As is apparent from the prior description, during the heart dilation period, the blood flowing through the coronary artery reaches the maximum value and the blood in the heart reaches the minimum value.

Then, the transmitter 9 shown in FIG. 2 generates a 90° pulse and a 180° pulse when the radio frequency controlling section 13 under the control of the sequence controller section 15 sends a control signal to the transmitter 9.

In FIG. 6(A), 157 denotes a 90° pulse and denotes a 180° pulse. These 90° and 180° pulse signals generate the NMR signal. This means that the NMR signal is generated when nuclear spins return to the original state. The NMR signal (spin echo signal) is denoted by 159.

A magnetic field gradient pulse for slice selection is denoted by 71. This pulse is applied in the direction of the z-axis, that is in, the direction of the patient's height.

The gradient magnetic field supply source 10 in FIG. 2 generates the magnetic field gradient 71 for slice selection under the control of the gradient magnetic field controlling section 17. The sequence controller section 15 determines when the magnetic field gradient pulse for slice selection is generated on the electrocardiogram waveform.

As shown in FIG. 6(A), 72 denotes a phase encode pulse which is a magnetic field gradient pulse for encoding a phase. For two-dimensional imaging, by changing the amplitude of the phase encode pulse, the NMR signals are repeatedly obtained, and then are Fourier-transformed with respect to the time and Gx. As a result, two-dimensional information thus a two-dimensional slice image be obtained. The phase encoding pulse is applied through the gradient magnetic field coil unit 3 when it receives a signal from the gradient magnetic field supply source 10 on the basis of the control of the gradient magnetic field controlling section 17 by the sequence controller section 15.

A pulse 73 is applied to compensate for the dephase caused by the first half of the magnetic field gradient pulse 74 for reading. The sum of the influence over the spin phase of both the pulse 73 and of the first half of the pulse 74 is reduced to zero with respect to a stationary spin, but is reduced to a linear function with respect to moving spins. The sequence in FIG. 6(A) is sensitive to the spin flow velocity, that is, the flow velocity of blood. The pulse 73 is called a flow encode pulse.

On the other hand, the magnetic field gradient pulse 75a and 75b in FIG. 6(B) are called flow cancelling pulses for the following reasons: the pulse 75a is used to reduce the sum of the influence over the phase of the moving spins for the following reasons: the pulse 75a is used to reduce the sum of the influence of the pulses 75a and 73 on the moving spins to zero and the pulse 75b is used to reduce the sum of the influence of the pulses 75b and 74 on the moving spins to zero. Thus, the sequence in FIG. 6(B) is insensitive to the spin flow velocity, that is, the flow velocity of blood.

As set forth above, in FIG. 6(A), the pulse 73 shifts the moving spin phase. The phase of the stationary spin is not shifted. The sequence in FIG. 6(B) is not influenced by the flow because of the cancelling pulses 75a and 75b.

The computer 22 shown in FIG. 2 subtracts an NMR signal obtained using the sequence in FIG. 6(A) from an NMR signal obtained using the sequence in FIG. 6(B). The result is sent to the graphic CRT controller section 19 through the bus 21, where it is used for imaging. As a result, the signal corresponding to the spins given when the blood stands still is cancelled and thus only the blood passing through the coronary artery during the dilation of the heart is portrayed using both the sequence that is sensitive to a blood flow velocity and the sequence is insensitive to it. It is possible to portray the coronary artery using physical parameters such as blood flow phase (time phase), blood flow direction, blood flow acceleration, eddy flow, laminar flow, or blood flow amount. The sequence that is sensitive to blood flow acceleration may employ a secondary flow encode pulse instead of the primary flow encode pulse 73 used in the foregoing embodiment.

The sequence that is sensitive to the blood flow phase may be formed as follows. As the blood flow increases, the phase changes greatly because the sequence senses the excessive change of a gradient magnetic field. By analyzing the phase, therefore, the direction of the blood flow can be known. It is, therefore, possible to suppress the NMR signal sent from the heart on the basis of the phase information and stress the NMR signal sent from the coronary artery, resulting only in the portrayal of the coronary artery.

The sequence that is sensitive to the eddy flow or laminar flow can be formed as follows. Dephasing is applied to the eddy flow. No dephasing is applied since the phase changes regularly. Dephasing or not is the key to distinguishing the eddy flow or laminar flow in blood. It is obvious that the foregoing embodiment may be modified or varied to various forms by a person having ordinary skills in the art. It is to be noted that the embodiment described above does not limit the scope of the invention.

What is claimed is:

1. A method for enabling imaging of a coronary artery of a living body using nuclear magnetic resonance, comprising the steps of:
   locating the living body in a magnetic field;
   detecting a cardiac cycle of the living body;
   determining a dilation phase of a heart of the living body on the basis of the detected cardiac cycle; and
   selectively generating a nuclear magnetic resonance signal for enabling imaging of the coronary artery during the determined dilation phase.

2. A method according to claim 1, wherein the cardiac cycle of the living body is detected by an electrocardiograph.

3. A method according to claim 1, wherein the step of determining a dilation phase includes determining when a difference between blood velocity in the coronary artery and blood velocity in a left ventricle of the heart is at a maximum.

4. A method according to claim 1, further comprising the step of imaging the coronary artery.

5. A method according to claim 1, wherein the step of selectively generating a nuclear magnetic resonance signal for enabling imaging of the coronary artery includes applying high frequency energy to the living body in the presence of a magnetic field gradient flow encoding pulse to obtain a first nuclear magnetic resonance signal sensitive to blood flow in the coronary artery when blood flow in a main artery is substantially stationary and applying high-frequency energy to the living body in the presence of a magnetic field gradient flow canceling pulse to obtain a second nuclear magnetic resonance signal which is insensitive to blood flow in the coronary artery and main artery, and obtaining a difference signal of the first and second nuclear magnetic resonance signals as the nuclear magnetic resonance signal for enabling imaging of the coronary artery.

6. A method for enabling imaging of a coronary artery of a living body using nuclear magnetic resonance, comprising the steps of:
   locating the living body in a static magnetic field;
   detecting a cardiac cycle of the living body;
   determining a dilation phase of a heart of the living body on the basis of the detected cardiac cycle;
   generating first and second nuclear magnetic resonance signals during the determined dilation phase, the first nuclear magnetic resonance signal having a component depending on blood flow in the coronary artery, the component being substantially absent from the second nuclear magnetic resonance signal; and
   determining a difference between the first and second nuclear magnetic resonance signals for obtaining a signal for enabling imaging of the coronary artery.

7. A method according to claim 6, wherein the component is one of phase, direction, velocity, acceleration, eddy flow, laminar flow, and flow rate of the blood flow in the coronary artery.

8. A method according to claim 6, wherein the cardiac cycle of the living body is detected by an electrocardiograph.

9. A method according to claim 6, wherein the step of determining a dilation phase includes determining when a difference between blood velocity in the coronary artery and blood velocity in a left ventricle of the heart is at a maximum.

10. A method according to claim 6, further comprising the step of imaging the coronary artery.

11. An apparatus for enabling imaging of a coronary artery of a living body using nuclear magnetic resonance, comprising:
    means for generating a static magnetic field;
    means for applying a magnetic field gradient to the living body in the presence of the static magnetic field;
    means for generating high-frequency energy;
    means for detecting a cardiac cycle of the living body;
    means responsive to the cardiac cycle detecting means for determining a dilation phase of a heart of the living body on the basis of the detected cardiac cycle; and
    means for applying the high-frequency energy to the living body in the presence of the magnetic field gradient during the determined dilation phase so as to selectively generate a nuclear magnetic resonance signal for enabling imaging of the coronary artery.

12. An apparatus according to claim 11, wherein the cardiac cycle detecting means comprises an electrocardiograph.

13. An apparatus according to claim 11, wherein the means for determining a dilation phase further determines when a difference between blood velocity in the coronary artery and blood velocity in a left ventricle of the heart is at a maximum.

14. An apparatus according to claim 11, further comprising means for imaging the coronary artery.

15. An apparatus according to claim 11, wherein the means for applying the high-frequency energy applies the high-frequency energy to the living body in the presence of a magnetic field gradient flow encoding pulse to obtain a first nuclear magnetic resonance signal sensitive to blood flow in the coronary artery when blood flow in a main artery is substantially stationary and applies the high-frequency energy to the living body in the presence of a magnetic field gradient flow canceling pulse to obtain a second nuclear magnetic resonance signal which is insensitive to blood flow in the coronary artery and main artery, and obtains a difference signal of the first and second nuclear magnetic resonance signals as the nuclear magnetic resonance signal for enabling imaging of the coronary artery.

16. An apparatus for enabling a coronary artery of a living body using nuclear magnetic resonance, comprising:
   means for generating a static magnetic field;
   means for applying a magnetic field gradient to the living body in the presence of the static magnetic field;
   means for generating high-frequency energy;
   means for detecting a cardiac cycle of the living body;
   means responsive to the cardiac cycle detecting means for determining a dilation phase of a heart of the living body on the basis oft he detected cardiac cycle;
   means for applying the high-frequency energy to the living body in the presence of the magnetic field gradient during the determined dilation phase so as to generate first and second nuclear magnetic resonance signals, the first nuclear magnetic resonance signal having a component depending on blood flow in the coronary artery, the component being substantially absent from the second nuclear magnetic resonance signal; and
   means for determining a difference between the first and second nuclear magnetic resonance signals so as to obtain a signal for enabling imaging of the coronary artery.

17. An apparatus according to claim 16, wherein the component is one of phase, direction, velocity, acceleration, eddy flow, laminar flow, and flow rate of the blood flow in the coronary artery.

18. An apparatus according to claim 16, wherein the cardiac cycle detecting means comprises an electrocardiograph.

19. An apparatus according to claim 16, wherein the means for determining a dilation phase further determines when a difference between blood velocity in the coronary artery and blood velocity in a left ventricle of the heart is at a maximum.

20. An apparatus according to claim 16, further comprising means for imaging the coronary artery.

* * * * *